US 9,493,389 B2

(12) United States Patent
Fogle, III et al.

(10) Patent No.: US 9,493,389 B2
(45) Date of Patent: *Nov. 15, 2016

(54) DICARBOXYLIC ACID PRODUCTION WITH ENHANCED ENERGY RECOVERY

(75) Inventors: Raymond Elbert Fogle, III, Johnson City, TN (US);
(Continued)

(73) Assignee: Grupo Petrotemex, S.A. de C.V., San Pedro Garza Garcia (MX)

( * ) Notice: Subject to any disclaimer, the term of this patent is extended or adjusted under 35 U.S.C. 154(b) by 0 days.

This patent is subject to a terminal disclaimer.

(21) Appl. No.: 12/556,107

(22) Filed: Sep. 9, 2009

(65) Prior Publication Data
US 2010/0113826 A1    May 6, 2010

Related U.S. Application Data

(60) Provisional application No. 61/110,248, filed on Oct. 31, 2008.

(51) Int. Cl.
*C07C 51/265*    (2006.01)

(52) U.S. Cl.
CPC .............. *C07C 51/265* (2013.01); *Y02P 20/51* (2015.11)

(58) Field of Classification Search
None
See application file for complete search history.

(56) References Cited

U.S. PATENT DOCUMENTS 3,541,802 A * 11/1970 Swearingen .................... 62/619
4,722,190 A    2/1988 Yamamoto et al.
(Continued)

FOREIGN PATENT DOCUMENTS

CN    1137266 A    12/1996
CN    1634848 A    7/2005
(Continued)

OTHER PUBLICATIONS

Copending U.S. Appl. No. 12/556,096, filed Sep. 9, 2009, Raymond Elbert Fogle, III, et al.
(Continued)

*Primary Examiner* — Sudhakar Katakam
*Assistant Examiner* — Jennifer C Sawyer
(74) *Attorney, Agent, or Firm* — Oblon, McClelland, Maier & Neustadt, L.L.P.

(57) ABSTRACT

The invention provides improved energy content in and shaft power recovery from off-gas from xylene oxidation reactions while at the same time minimizing wastewater treatment cost. More shaft power is produced using off-gas than is required to drive the main air compressor, even with preferred, relatively low oxidation temperatures. Simultaneously, an amount of wastewater greater than byproduct water from oxidation of xylene is kept in vapor form and treated along with off-gas pollutants in a self-sustaining (self-fueling) gas-phase thermal oxidative destruction unit. Optionally, off-gas is combined from multiple xylene oxidation reactors, comprising primary and/or secondary oxidation reactors and forming TPA and/or IPA. Optionally, air compressor condensate and caustic scrubber blowdown are used in a TPA process or as utility water, effectively eliminating normal flow of liquid wastewater effluent from a TPA plant. Optionally, PET off-gas containing the water of PET formation is treated in a shared thermal oxidative destruction unit, effectively eliminating normal flow of liquid wastewater effluent from a combined pX-to-TPA-to-PET plant.

28 Claims, 1 Drawing Sheet

(75) Inventors: Ronald Buford Sheppard, Kingsport, TN (US); Timothy Alan Upshaw, Kingsport, TN (US); Alan George Wonders, Longview, TX (US)

(56) References Cited

U.S. PATENT DOCUMENTS

| | | | |
|---|---|---|---|
| 4,939,297 | A | 7/1990 | Browder et al. |
| 5,612,007 | A | 3/1997 | Abrams |
| 5,614,159 | A | 3/1997 | Modic et al. |
| 5,723,656 | A | 3/1998 | Abrams |
| 5,961,942 | A * | 10/1999 | Turner et al. ............ 423/240 S |
| 6,137,001 | A | 10/2000 | Broeker et al. |
| 6,504,051 | B1 | 1/2003 | Miller, Jr. et al. |
| 7,049,465 | B2 | 5/2006 | Lin |
| 7,351,396 | B2 | 4/2008 | Lin et al. |
| 2002/0193629 | A1* | 12/2002 | Miller et al. ................. 562/412 |
| 2005/0038288 | A1 | 2/2005 | Lin et al. |
| 2006/0047158 | A1 | 3/2006 | Wonders et al. |
| 2007/0155985 | A1 | 7/2007 | Wonders et al. |
| 2007/0208190 | A1 | 9/2007 | Wonders et al. |
| 2007/0208191 | A1 | 9/2007 | Wonders et al. |
| 2007/0219393 | A1 | 9/2007 | Lin et al. |
| 2007/0276155 | A1 | 11/2007 | Upshaw et al. |
| 2007/0293699 | A1 | 12/2007 | Wonders et al. |
| 2008/0097118 | A1 | 4/2008 | Bartos et al. |
| 2008/0194865 | A1 | 8/2008 | Bartos |
| 2010/0113826 | A1 | 5/2010 | Fogle, III et al. |

FOREIGN PATENT DOCUMENTS

| | | | |
|---|---|---|---|
| EP | 1262523 | A1 | 12/2002 |
| EP | 1939236 | A1 | 7/2008 |
| EP | 2 349 971 | | 6/2010 |
| JP | 11-349530 | A | 12/1999 |
| JP | 2004-257606 | A | 9/2004 |
| JP | 2006-249106 | A | 9/2006 |
| KR | 100397242 | B1 | 3/2004 |
| WO | WO 96/11899 | A1 | 4/1996 |
| WO | 9727168 | A1 | 7/1997 |
| WO | 9941221 | A1 | 8/1999 |
| WO | 9962857 | A1 | 12/1999 |
| WO | 2006102137 | A1 | 9/2006 |

OTHER PUBLICATIONS

Copending U.S. Appl. No. 12/556,099, filed Sep. 9, 2009, Raymond Elbert Fogle, III, et al.
Copending U.S. Appl. No. 12/556,101, filed Sep. 9, 2009, Raymond Elbert Fogle, III, et al.
Copending U.S. Appl. No. 12/556,103, filed Sep. 9, 2009, Raymond Elbert Fogle, III, et al.
Search Report and Written Opinion issued Jan. 8, 2013 in Singaporean Application No. 201102696-0.
Mexican Office Action Issued Jan. 2, 2013 in Patent Application No. MX/a/2011/004495.
Office Action issued Mar. 20, 2013 in Chinese Patent Application No. 200980143798.2 (with English translation).
European Office Action issued Jun. 14, 2011, in Patent Application No. 09745152.0.
International Preliminary Report on Patentability and Written Opinion of the International Searching Authority issued May 3, 2011, in Patent Application No. PCT/US2009/005764.
Office Action issued Nov. 26, 2013 in Japanese Patent Application No. 2011-534498 (submitting English translation only).
Office Action issued Nov. 18, 2014, in Japanese Patent Application No. 2011-534498, filed Oct. 22, 2009 w/attached English translation.
Office Action issued Dec. 23, 2014, in Indian Patent Application No. 3059/DELNP/2011, filed Apr. 27, 2011.
Office Action issued Aug. 7, 2013 in Russian Patent Application No. 2011121840/4 submitting English translation only.
Office Action issued Apr. 29, 2016 in Korean Patent Application No. 10-2011-7012497 (with English translation).
Canadian Office Action issued Nov. 16, 2015, in corresponding Canadian Application No. 2,741,636.
Office Action issued Dec. 18, 2015 in Japanese Patent Application No. 2015-055315 (with English language translation).

* cited by examiner

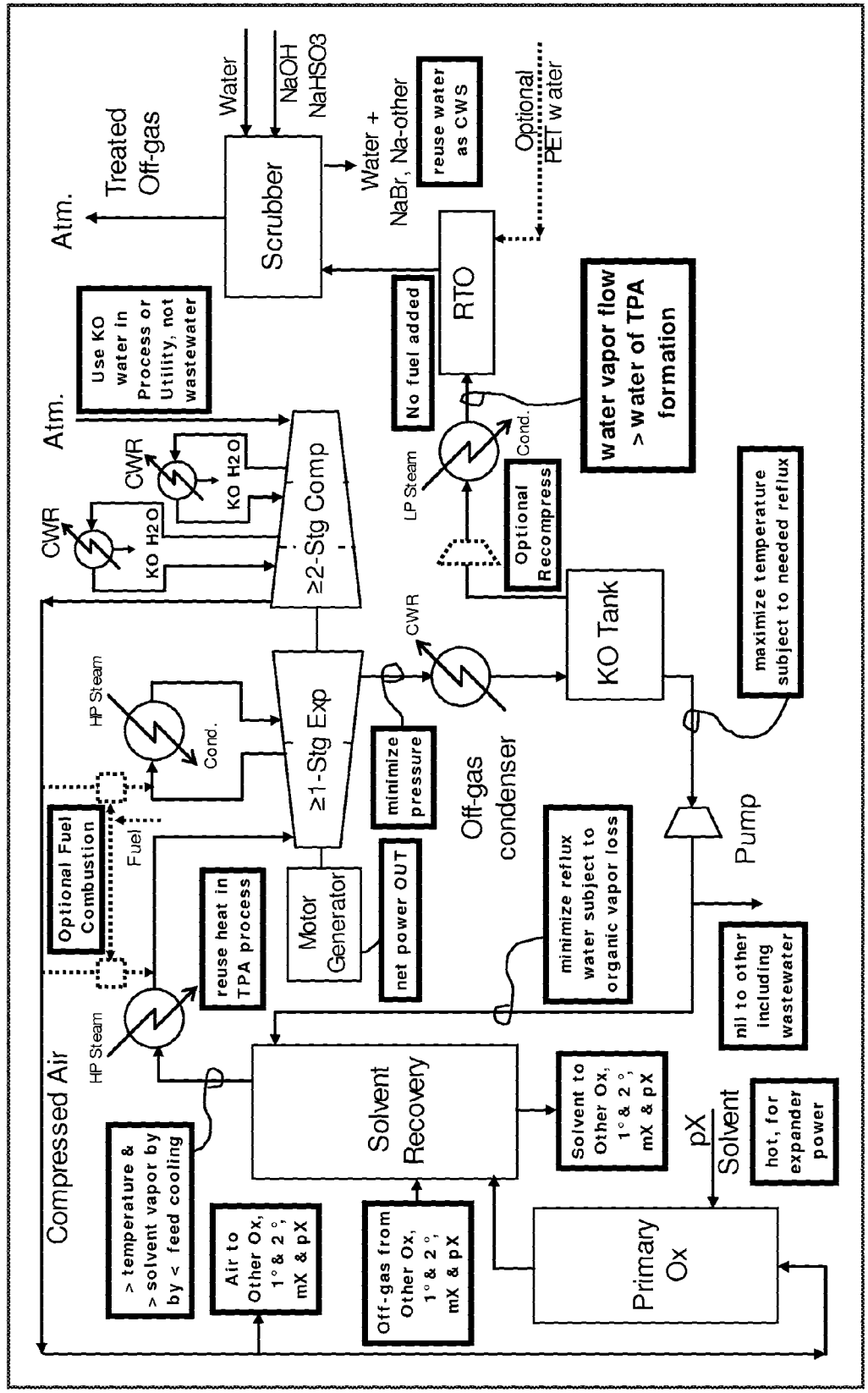

DICARBOXYLIC ACID PRODUCTION WITH ENHANCED ENERGY RECOVERY

CROSS-REFERENCE TO RELATED APPLICATIONS

This application claims priority to U.S. Provisional Application Ser. No. 61/110,248, filed on Oct. 31, 2008, the disclosure of which is incorporated herein by reference in its entirety.

BACKGROUND

It is known to recover the preponderance of vaporized solvent from reaction off-gas by passing it through at least one cooling, absorbing, and/or distillation means to produce a liquefied recovered solvent. It is generally desirable to maximize the recovery from reaction off-gas of vaporized compounds containing at least one hydrocarbyl bond, herein called "hydrocarbyl compounds," "volatile organic compounds," and "VOC".

It is known to use at least one distillation means to remove from recovered solvent an amount of excess water, which is coproduced in large quantities by the partial oxidation of pX. Various designs are known for using energy derived from the partial oxidation of pX for at least a portion of the energy input required to operate a distillation means.

The term "water of TPA formation" is defined herein as 0.340 kilogram of water per kilogram of commercial purity pX feed. This comes from the intended reaction forming TPA from pX according to the stoichiometry: $pX+3O_2$ yields $TPA+2H_2O$. Notwithstanding that small amounts of impurities exist within commercial purity pX and that a small amount of pX is under-oxidized and/or over-oxidized, modern manufacturing facilities produce commercial purity pX comprising very low amounts of impurities and to convert such feed into crude and/or purified TPA with very high yields. Preferably the overall yield of TPA solid product, crude and/or purified, is at least about 96, or 97, or 98, or 99 mole percent based on the mass of commercial purity pX feed divided by a molecular weight of 106.16 grams per mole. Preferably, the commercial purity pX feed comprises at least about 0.990, or 0.995, 0.997, or 0.998 mass fraction of pX.

It is also known to recover energy, both thermal energy and mechanical shaft work, from a portion of off-gas in various combinations along with recovery of vaporized solvent. One known method for energy recovery is to use at least a portion of off-gas to boil a working fluid, e.g., water or pentane, to produce a vapor. This vapor is used to transfer heat to another user, or the vapor is reduced in pressure through an expander, typically a turboexpander, to produce shaft work output. The energy recovery from a turboexpander can be converted directly to mechanical work, such as driving an air supply compressor or other moving machinery, or to electrical power by driving a rotating electrical generator connected to a power distribution and consuming network.

Another known method for energy recovery is to pass at least a portion of the off-gas comprising dinitrogen through a turboexpander. The energy recovery from a turboexpander can be converted directly to mechanical work, such as driving an air supply compressor or other moving machinery, or to electrical power by driving a rotating electrical generator connected to a power distribution and consuming network.

It is also known to send a significant portion of water in vapor form in the off-gas to a thermal oxidative destruction means (TOD) wherein noxious gaseous and VOC pollutants, e.g., carbon monoxide, acetic acid, methyl acetate, para-xylene, and methyl bromide, are converted to more environmentally acceptable effluents, e.g., water vapor and carbon dioxide. Certain convention systems disclose expelling "the water of reaction" in vapor form from a para-xylene oxidation reactor into a thermal destruction device for removal of noxious pollutants.

SUMMARY

The inventors have discovered preferred embodiments not contemplated in the prior art. Embodiments of the present invention can provide a greater amount of shaft work power recovery from reaction off-gas of certain oxidation reaction media, whether to electrical power generation or directly to mechanical uses, and/or expelling an amount water vapor even greater than the water of TPA formation, and/or a self-sustaining (self-fueling) TOD. Certain embodiments of the invention can even provide a combined facility for pX-to-TPA-to-PET that produces effectively no liquid wastewater.

In a preferred embodiment, the invention comprises passing substantially all of the oxidation reaction off-gas, including both primary and secondary oxidation reactor sources with both pX and mX feeds, through a shared solvent recovery distillation system, then through a superheating step, and then through a 2-stage turboexpander comprising interstage heating in order to produce a greater amount of shaft-work. This configuration allows exporting electrical power beyond the consumption of the process air compressors and process liquid and slurry pumps. Flash steam from condensate in the turboexpander heaters is used in another portion of the TPA process. After the turboexpander, a portion of the water vapor is condensed from the oxidation reaction off-gas to provide liquid water for various process uses; and the balance of the water vapor is left in the off-gas, which is sent to a TOD means. Optionally, direct fuel firing is used to heat off-gas, rather than steam heating, to provide superheat within a turboexpander. Optionally, the outlet pressure of a turboexpander is reduced by recompressing off-gas after it has passed though a condenser means and liquid knock-out means.

Furthermore, the following embodiments are preferred for other aspects of the inventive process:

It is preferred that enough combustible fuel value is left in off-gas such that its environmental abatement in a TOD, preferably a Regenerative Thermal Oxidizer (RTO), is substantially, more preferably completely, self-heating without addition of fuels not present in the reaction off-gas. It is still more preferred that a substantial amount of this combustible fuel value comes from methyl acetate (MeOAc), a known byproduct of oxidation of pX in acetic acid. The inventors have discovered how to keep formation of methyl acetate sufficiently low such that the considerable capital and operating cost to isolate the methyl acetate and to recover by hydrolysis the acetic acid content are not justified when considered against adding purchased fuel to a RTO.

Condensed water is often formed from ambient water vapor in compression systems providing ambient air to TPA oxidation reactors, and this water is potentially contaminated with lubricants and seal fluids. It is preferred that this condensed ambient water is admitted to TPA process liquids, e.g., as scrubber water, quench water, reflux water, or is used as utility water, e.g., as cooling tower makeup water, rather than being sent directly to a liquid wastewater treatment facility.

After removal and/or thermal destruction of VOC in off-gas, many locales require removal of hydrogen bromide from such treated off-gas before release to ambient. This scrubbing is often done by aqueous scrubbing to produce a bromine salt, e.g., using an aqueous solution of sodium hydroxide and sodium bisulfite to scrub and to produce sodium bromide. The inventors have discovered that blowdown water used to control the dissolved solids content in such scrubber water is advantageously used as utility water, e.g., cooling tower makeup water, rather than forming liquid wastewater.

A PET process also produces water from PET formation reactions, and this water is often contaminated with various VOC compounds, e.g., ethylene glycol, acetaldehyde, and various dioxolanes. It is preferred that at least a portion of contaminated water from a PET process is processed in a shared, common facility along with water of TPA formation from an adjacent TPA facility. Preferably, said contaminated water from PET formation is either left in vapor form exiting said PET facility for treatment or it is converted to a vapor form using at least a portion of thermal energy from said adjacent TPA facility. More preferably water from PET formation reactions is processed in a shared, common TOD along with water of TPA formation.

Alone, or in various combinations, the inventions disclosed herein can provide a pX-to-TPA facility producing very low, even nil, liquid wastewater requiring environmental treatment per unit of TPA production. Further, the inventions can provide a pX-to-TPA-to-PET facility producing very low, even nil, liquid wastewater requiring environmental treatment per unit of PET production.

BRIEF DESCRIPTION OF THE DRAWINGS

FIG. 1 illustrates exemplary embodiments of the present invention.

DETAILED DESCRIPTION OF THE PREFERRED EMBODIMENTS

The inventions herein can be combined with the disclosures of US 20070293699 and US 20060047158 (the entire disclosures of which are incorporated herein by reference) for a preferred primary oxidation reaction medium, process, and means for converting pX to TPA, with a preferred oxidizer reactor being a bubble column reactor. These reference disclosures comprise numerous preferred mechanical features and process conditions for a primary oxidation, with process conditions notably including temperatures and gradients, pressures and gradients, flows, compositions and gradients, agitation, and residence times and distributions. The usages herein for "oxidizable compound", "solvent", "oxidant", "reaction medium", and "hydrocarbyl" are accordingto the above references.

The inventions herein are more preferred when at least a portion of off-gas from a secondary oxidation reaction medium is combined with at least a portion off-gas from a primary oxidation reaction medium before processing in a solvent recovery and/or dehydration means. A secondary reaction medium is one receiving most of its feed of aromatic substrate from an upstream oxidation reactor which may be a primary oxidation reaction medium and/or another secondary reaction medium. See US 20070155985 and US 20070208191 for descriptions of a secondary oxidization reactor optimized around further reaction of the entering liquid-phase aromatic substrate, including benefits of operating in selected process ranges comprising temperatures, pressures, flows, compositions, agitation, and residence times and distributions, balanced against various costs, notably including over-oxidation of substrate, product, and solvent. Herein, this type of secondary oxidation reactor is referred to as a "post-oxidation reactor." Also, see US 20070208190 and US 20070219393 for descriptions of a secondary oxidization reactor optimized around further reaction of the entering solid-phase aromatic substrate, including benefits of operating in selected process ranges comprising temperatures, pressures, flows, compositions, agitation, and residence times and distributions, balanced against various costs, notably including over-oxidation of substrate, product, and solvent. Herein, this type of secondary oxidation reactor is referred to as a "digestion reactor".

When intentionally producing power, especially shaft power, by combusting (oxidatively burning) compounds essentially comprising hydrocarbyl bonds (fuels), the temperature of said combusting is often pushed as high as mechanically practicable in order to maximize power recovery according to known thermodynamic principles. On the other hand, when conducting a catalytic partial oxidation to form a chemical product, the temperature and pressure of reaction medium is ordinarily set to control the resulting yields, conversions, and product purities. Catalytic oxidations of the present invention are sufficiently rapid that great care is required to maintain suitable liquid-phase concentrations of dissolved dioxygen, and this causes a preference for higher system pressures to provide higher partial pressures of gas-phase dioxygen.

Despite these general preferences for higher temperature for energy recovery and for higher pressure for TPA product purity, the inventors have discovered that it is preferred to operate at least a portion of a primary oxidation reaction medium with the following moderate pressures and temperatures, even while recovering an improved amount of shaft power and even while expelling greater amounts of wastewater in vapor form. It is preferred to operate at least a portion of primary oxidation reaction medium with a pressure of less than about 12, 10, 8, 7 bara. It is preferred to operate at least a portion of primary oxidation reaction medium with a pressure of at least about 2, or 3, or 4, or 5 bara. It is preferred to operate at least a portion of primary oxidation reaction medium with a temperature of less than about 200, or 190, or 180, or 170° C. It is preferred to operate at least a portion of primary oxidation reaction medium with a temperature of at least about 120, or 130, or 140, or 150° C., or 155° C., or 160° C.

The inventors have discovered that it is preferred to generate the greatest volumes and masses of vapor possible at the exit of off-gas from reaction medium while satisfying the energy balance as required to obtain preferred reaction temperatures and pressures. Undesirably, the generation of larger amounts of vapor increases the difficulty in disengaging liquids and solids from the off-gas exiting a reaction medium. Undesirably, such an increase in off-gas enlarges the diameters and volumes of conduits and equipment processing reaction off-gas; this notably includes a solvent recovery and/or dehydration means. Undesirably, the oxidation reaction medium of the present invention produces an off-gas that is sufficiently corrosive to require unusually expensive materials of construction, often comprising titanium. Undesirably, the increased flow of vapor exiting reaction medium is greatly attenuated in both mass and volume during processing in a solvent recovery and/or dehydration means, wherein the preponderance of the hydrocarbyl portion of solvent is recovered. However, the inventors have discovered that an increased amount of solvent vapor formed in reaction off-gas can be sustained in part as an increased amount of vapor, essentially comprising water, exiting a solvent recovery and/or dehydration means and entering an off-gas turboexpander, often providing an overall economic advantage in shaft energy recovery that surprisingly outweighs the increases in other operating costs and the increases in capital cost. In an embodiment of the present invention the hydrocarbyl-depleted off-gas produced from solvent recovery column comprises at least 10, or 15, or 20, or 30, or 35, or 40, or 45, or 50 wt % water vapor based on the hydrocarbyl-depleted off-gas stream. In another embodiment of the invention the hydrocarbyl-depleted off-gas produced from the solvent recovery column comprises less than 4, or 3, or 2, or 1 wt % acetic acid based on the hydrocarbyl-depleted off-gas stream.

The vapor compounds in reaction off-gas comprise water vapor plus VOC. Non-condensable gaseous compounds in reaction off-gas comprise dinitrogen, dioxygen, carbon monoxide, carbon dioxide, and dihydrogen. Applying various aspects of the present invention, the inventors have discovered that it is possible and preferred to operate a pX partial oxidation process with increased amounts of vapor compounds in reaction off-gas as follows. It is preferred that the vapor compounds in a reaction off-gas are at least about 0.67, or 0.72, or 0.75, or 0.77 kilograms per kilogram of reaction off-gas. It is preferred that the vapor compounds in a reaction off-gas are at least about 12.4, or 13.2, or 13.8, or 14.2 kilograms per kilogram of pX fed to corresponding oxidation reaction medium.

To achieve such great amounts of vapor in reaction off-gas, the inventors have discovered that it is preferred to suppress greatly the ambient losses and intentional heat removal from an oxidation reaction medium of the present invention across conductive, isolating, boundary surfaces, despite that such oxidation reaction is highly exothermic and requires great cooling. It is preferred to insulate such that at least about 70, or 90, or 95, or 99 percent of the exposed, ambient surface area of vessels and/or conduits containing at least a portion of oxidation reaction medium are covered with at least about 0.01, or 0.02, or 0.04, or 0.08 meters thickness of insulation material. It is preferred that thermal energy losses through exposed, ambient surface area of conduits and/or vessels containing at least a portion of oxidation reaction medium are less than about 40, or 20, or 10, or 5 watts per kilogram of pX fed to corresponding oxidation reaction medium. It is preferred to limit cooling of at least a portion of oxidation reaction medium by utility cooling fluids, e.g., water and air, through conductive, isolating, heat-exchange boundary surfaces such that thermal energy removal is less than about 100, or 10, or 0.1, or 0.01 watts per kilogram of pX fed to corresponding oxidation reaction medium.

To achieve such great amounts of vapor in reaction off-gas, the inventors have furthermore discovered it is preferred that feeds to an oxidation reaction medium are as hot as practicable, again despite that such oxidation reaction is highly exothermic and requires great cooling. It is preferred that oxidant feed to at least one oxidation reaction medium is compressed air wherein cooling is minimized after exiting final stage of compression. It is preferred that at least about 50, or 70, 90, or 99 percent of the mass of said compressed air reaches an oxidation reaction medium with a temperature at least about 60, 70, 80, 90° C. It is preferred that at least about 50, or 70, or 90, or 99 percent of the mass of said compressed air reaches an oxidation reaction medium with a temperature of at least about the discharge temperature of a corresponding air compressor minus 40, or 20, or 10, or 5° C. It is preferred to insulate such that at least about 50, or 70, or 90, or 95 percent of the exposed, ambient surface area of conduits, vessels, and controls for delivering said compressed air are covered with at least about 0.005, or 0.01, or 0.02, or 0.04 meters thickness of insulation.

It is preferred that solvent is recovered from reaction off-gas in at least one solvent recovery and/or dehydration means and then returned to an oxidation reaction medium with a temperature that is above ambient temperature and near the temperature of corresponding reaction medium. That is, it is preferred that hydrocarbyl compounds are condensed from reaction off-gas, appropriately dehydrated, and returned to reaction medium without being much cooler than reaction off-gas. More preferably, this hot recovered solvent is provided with limited amounts of thermal energy input through conductive, isolating, heat-exchange boundary surfaces. As is disclosed elsewhere herein, this result is achieved by appropriately limiting the amount of thermal energy removed in said solvent recovery and/or dehydration means. It is preferred that at least about 40, or 60, or 80, or 90 weight percent of said recovered solvent is supplied to an oxidation reaction medium with a temperature of less than about 200, or 190, or 180, or 170° C., since it is preferred not to transfer thermal energy into recovered solvent at a temperature greater than the temperature of the primary oxidation reaction medium. It is preferred that at least about 40, or 60, or 80, or 90 weight percent of said recovered solvent is supplied to an oxidation reaction medium with a temperature of at least about reaction off-gas temperature minus less than about 80, or 40, or 20, or 10° C. It is preferred that at least about 40, or 60, or 80, or 90 weight percent of said recovered solvent is supplied to an oxidation reaction medium with a temperature of at least about 60, or 90, or 120, or 140° C. It is preferred that at least about 40, or 80, or 90, or 98 percent of the net thermal energy input to a solvent recovery and/or dehydration means comes directly from the entering flow of reaction off-gas without thermal energy transfer through conductive, isolating, heat-exchange boundary surfaces. It is preferred that at least about 40, or 60, or 80, or 90 weight percent of said recovered solvent exits a solvent recovery and/or dehydration means with a temperature of at least about the temperature of corresponding reaction off-gas minus less than about 80, or 40, or 20, or 10° C. while being processed therein using a thermal energy input through conductive, isolating, heat-exchange boundary surfaces of less than about 100, or 30, or 10, or 3 kilocalorie per kilogram of recovered solvent enters a corresponding reaction medium with a thermal energy input through conductive, isolating, heat-exchange boundary surfaces of less than about 100, or 30, or 10, or 3 kilocalories per kilogram of recovered solvent. It is preferred to insulate such that at least about 70, or 90, or 95, or 99 percent of the exposed, ambient surface area of vessels and/or conduits containing at least a portion of recovered solvent are covered with at least about 0.01, or 0.02, or 0.04, or 0.08 meters thickness of insulation material.

It is preferred that filtrate solvent recovered from filtration and washing of solid TPA is returned to an oxidation reaction medium with elevated temperature provided by transfer of thermal energy through conductive, isolating, heat-exchange boundary surfaces. Filtrate solvent is solvent from mechanical separation and/or/or washing of solid TPA from a slurry. One means for obtaining filtrate solvent is filtration and washing of TPA slurry by any means known in the filtration art, but all other mechanical separations known in the art are contemplated by the inventors for producing filtrate solvent; e.g., gravity settling, centrifuges, hydroclones, and the like.

Before returning to an oxidation reaction medium, it is preferred to cool at least about 40, or 60, or 70, or 80 weight percent of said filtrate solvent to a temperature of less than about 100, or 80, or 70, or 60° C. This usefully reduces the solubility of TPA in the slurry, and it usefully reduces the corrosivity of the filtrate solvent so that less expensive materials of construction may be used for conduits, vessels, pumps, and other equipment and controls comprising the storage and processing of filtrate solvent. Suitable materials of construction for said cooled filtrate solvent comprise various metals and alloys with moderate corrosion resistance, such as stainless steels or duplex steels, as alternatives to titanium and other more expensive, highly corrosion resistant metals and alloys.

However, it is more preferred that at least about 40, or 60, or 70, or 80 weight percent of said filtrate solvent is provided to oxidation reaction medium with an inlet temperature of at least about 60, or 90, or 120, or 140° C. It is preferred to use solar energy, thermal energy from off-gas, and/or thermal energy from steam condensing at a pressure of less than about 60, or 20, or 8, or 4 bara to heat about 40, or 60, or 70, or 80 weight percent of said filtrate solvent by at least about 10, or 20, or 40, or 60° C. before feeding into an oxidation reaction medium. It is preferred to transfer this thermal energy into filtrate solvent through conductive, isolating, heat-exchange boundary surfaces.

It is preferred that pX is fed to an oxidation reaction medium with elevated temperature. It is preferred that at least about 40, or 60, or 70, or 80 weight percent of said pX feed is provided to a reaction medium with an inlet temperature of at least about 60, or 90, or 120, or 140° C. It is preferred to use solar energy, thermal energy from off-gas, and/or thermal energy from steam condensing at a pressure of less than about 60, or 20, or 8, or 4 bara to heat about 40, or 60, or 70, or 80 weight percent of said pX by at least about 10, or 20, or 40, or 60° C. above bulk storage and/or ambient temperature before feeding into an oxidation reaction medium. It is preferred to transfer this thermal energy into pX through conductive, isolating, heat-exchange boundary surfaces Separately or in combination, the hotter feeding temperatures of compressed air, recovered solvent, filtrate solvent, and/or pX require supplying increased liquid flow into an oxidation reactor in order to maintain its energy balance in order to achieve preferred operating temperatures and pressures. With hotter feeds, more of the heat of reaction is removed as latent heat of solvent vaporization, rather than sensible heating of feeds, and an increased amount of liquid solvent feed exits the oxidation reactor as solvent vapor in reaction off-gas. Undesirably, supplying increased amounts of liquid solvent feed requires more costly pumps, conduits, and controls along with increased amounts of pumping power.

For compression of ambient air, elevating supply temperatures by omitting an after-cooler often increases the amount of water vapor entering the oxidation process, unless a desiccating means is provided different from cooling. Such added water must eventually be separated and expelled from the oxidation process along with the water of TPA formation in order to maintain the desired solvent composition. Furthermore, when such added water is eventually expelled, whether as vapor or liquid or solid, some purchased, carbon-containing mass is often lost coincidentally, and an added wastewater load is eventually created according to prior art. Thus, such additional entering water vapor in compressed ambient air may be viewed as doubly undesirable, creating a potential carbon loss and a wastewater increase.

However, by using inventions disclosed elsewhere herein to expel increased amounts of water as vapor and to use limited, coincident amounts of VOC as combustion fuel in a TOD, the inventors have discovered a net, positive benefit for leaving selected amounts of water vapor in compressed ambient air used for oxidant feed. Accordingly, it is preferred that at least about 70, or 80, or 90, or 95 weight percent of oxidant feed to at least one oxidation reaction medium of the present invention comprises at least about 0.01, or 0.03, or 0.04, or 0.05 kilogram of water per kilogram of pX fed to corresponding oxidation reaction medium and less than about 0.12, or 0.10, or 0.08, or 0.07 kilogram of water per kilogram of pX fed to corresponding oxidation reaction medium.

After exiting an oxidation reaction medium, more preferably a primary oxidation reaction medium, it is preferred to use at least a portion of off-gas to generate an amount of shaft work using one or more turboexpander means. A turboexpander means, or simply turboexpander, is one or more turboexpander steps staged in series, optionally with one or more interstage heating means. The off-gas exiting the lowest pressure stage of a turboexpander, prior to further process steps, is referred to herein as turboexpander off-gas. It is preferred to locate at least one turboexpander step such that it is mechanically linked to at least one compression step for supply of oxidant from ambient air. Such linkage is conveniently provided by a rotating mechanical shaft and/or gearbox.

In order to maximize shaft power, it is desirable to minimize the loss of pressure and thermal energy from off-gas before entering a turboexpander. However, there are competing demands for consumption of pressure and temperature energy in order to recover solvent and to remove appropriate amounts of water in a solvent recovery and/or dehydration means. Also, capital cost requirements for a solvent recovery and/or dehydration means increase greatly at the reduced pressures preferred for the outlet of a turboexpander means, for the volumes of off-gas become exceedingly large.

As disclosed herein, the inventors have discovered combinations of features that enable and balance the consumption of pressure and temperature energy from reaction off-gas in a solvent recovery and/or dehydration means against the recovery of shaft power from off-gas in a turboexpander means. Discoveries and enabling disclosures for a preferred solvent recovery and/or dehydration means are contained elsewhere herein. Before proceeding to them, the preferred aspects pertaining to a turboexpander means are disclosed.

Attention is directed to the preferred pressure ranges pertaining to inlets flows to turboexpander steps. It is preferred that the pressure at the off-gas outlet from a solvent recovery and/or dehydration means is reduced by less than about 2, or 1, or 0.5, or 0.2 bar static pressure evaluated from where reaction off-gas is formed near an upper surface of reaction medium. It is preferred that the frictional flowing pressure loss through an optional heating means providing thermal energy to off-gas between an outlet of a solvent recovery and/or dehydration means and an inlet of a turboexpander is less than about 32,000, or 16,000, or 8,000, or 4,000 Pascal. It is preferred that the pressure of off-gas at an inlet to a first turboexpander step is reduced by less than about 2, or 1, or 0.5, or 0.2 bar static pressure evaluated from where reaction off-gas is formed near an upper surface of reaction medium. It is preferred that the pressure at the inlet to at least on turboexpander step is at least about 2, or 3, or 4, or 5 bara. It is preferred that the pressure at the inlet to a first turboexpander step is less than about 12, or 10, or 8, or 7 bara. It is preferred that flowing frictional pressure loss in any interstage conduits and process steps, such as heat exchange means, summed between the inlet to a first stage of turboexpander and the outlet of a last stage is less than about 64,000, or 32,000 or 16,000, or 8,000 Pascal.

Although it is desirable to minimize the distance from the off-gas exit from solvent recovery and/or dehydration means to the inlet of a turboexpander in order to minimize the loss of thermal energy out through insulation and the loss of pressure energy by flowing frictional loss, the inventors have discovered that it is preferred to locate the off-gas inlet to a turboexpander within less than about 40, or 30, or 20, or 10 meters measured upwards from surrounding grade. This maximizes the reconversion of the elevation head of off-gas into static pressure at the inlet of the turboexpander, since the elevation of off-gas exiting solvent recovery and/or dehydration means can be greater than 50 meters above grade.

For greater recovery of shaft power, it is preferred to minimize the back-pressure on a turboexpander. Reduced back-pressure helps to maximize shaft power recovery with a turboexpander by maximizing the decompression ratio and volume of exiting gas. However, turboexpander off-gas of the present invention has other competing needs. At the very least, pressure must be provided for flow through conduits, controls, and various equipment, often comprising a condensing means and an environment treatment means, before release to ambient surroundings. Producing turboexpander off-gas at lower pressures causes considerable difficulties with designs and capital cost in these downstream processes. A greater pressure for turboexpander off-gas is indicated for ease in condensing preferred amounts of water and VOC, especially in those process designs preferring to condense (substantially) "all" of the water vapor in expander off-gas. With lower pressures, condensing appropriate portions of the water vapor and VOC from turboexpander off-gas is difficult or impossible to achieve using utility cooling fluids with near-ambient temperatures, and refrigerating utility cooling fluids is undesirable for such large heat duties. Also, the required physical size for a heat exchange means is reduced if more pressure is retained in turboexpander off-gas, owing to improved heat exchange coefficients, to improved temperature differential with any given utility cooling fluid supply temperature, and to managing velocities, pressure drop, and flow distribution within said heat exchange means. Even after condensing a majority or even preponderance of water vapor and VOC, lower pressures for turboexpander off-gas continue to mean larger sizes for further downstream conduits, controls, and equipment. Furthermore, some process designs prefer to use expander off-gas or condenser off-gas to convey TPA product powder, and this may cause another need for increased turboexpander back-pressure.

According to one aspect of the present invention, the inventors have discovered that the disclosed designs for off-gas conduits, controls, heat exchanger means, TOD means, and scrubber means enable the following preferred pressure conditions at the outlet of an off-gas turboexpander. It is preferred that the pressure of turboexpander off-gas is less than about 0.9, or 0.6, or 0.4, or 0.3 bar gauge. It is preferred that the pressure of turboexpander off-gas is at least about 0.05, or 0.10, or 0.15, or 0.20 bar gauge, with this aspect providing enough pressure energy to flow turboexpander off-gas through disclosed conduits, controls, and equipment and comprising off-gas condenser, condensate demisting and demisting, TOD, and scrubber, while not comprising a re-compression step, before release to ambient surroundings.

According to another aspect of the present invention, it is preferred to minimize further the turboexpander back-pressure by minimizing the downstream pressure usage as above and by also providing an off-gas recompression step located after a condenser heat exchange means wherein at least about 10, or 20, or 40, or 80 weight percent of the water vapor present in turboexpander off-gas is removed as liquid water. The inventors have discovered that, even while venting water vapor to ambient surroundings according to the inventions herein, efficient removal of water vapor from off-gas according to inventions herein enables a recompression step for the remaining off-gas that requires usefully less power than the increase in power provided by the greater decompression in an upstream turboexpander. In addition, it is more preferable to locate a knock-out means between an off-gas condenser means and the inlet to a recompression means. (See elsewhere herein for disclosures and designations for condenser off-gas and knock-out off-gas.) When using off-gas recompression, it is preferred to recompress condenser off-gas, more preferably knock-out off-gas, by at least about 0.05, or 0.1, or 0.2, or 0.3 bar. When using off-gas recompression, it is preferred to recompress condenser off-gas, more preferably knock-out off-gas, by less than about 0.9, or 0.8, or 0.7, or 0.6 bar. When using off-gas recompression, it is preferred that the pressure of off-gas exiting the lowest pressure stage of a turboexpander is less than about 0.3, or 0.2, or 0.1, or 0.0 bar gauge. When using off-gas recompression, it is preferred that the pressure of off-gas exiting the lowest pressure stage of a turboexpander is at least about −0.9, or −0.6, or −0.4, or −0.3 bar gauge. When using off-gas recompression, it is preferred to locate at least one recompression step such that it is mechanically linked to at least one turboexpander step and/or at least one compression step for supply of oxidant from ambient air. Such linkage is conveniently provided by a rotating mechanical shaft and/or gearbox.

Attention is now directed to the preferred temperatures for an off-gas inlet to a turboexpander means or, if optionally provided, at the inlet of an off-gas preheating means placed after a solvent recovery and/or dehydration means and before said turboexpander means. It is preferred that the temperature at the inlet to a first turboexpander step is at least about 110, or 120, or 130, or 135° C., evaluated before any off-gas preheating means optionally placed ahead of a first turboexpander means. It is preferred that the temperature at the inlet to a first turboexpander step is less than about 190, or 175, or 165, or 155° C., evaluated before any off-gas preheating means placed ahead of a first turboexpander means. It is preferred that the temperature reduction evaluated from where reaction off-gas is formed near an upper surface of reaction medium to where off-gas enters a first turboexpander means, is less than about a 50, or 40, or 30, or 25° C. reduction, evaluated before any off-gas preheating means optionally placed ahead of a first turboexpander means.

Although condensing turboexpanders operating at or below the dewpoint of a working fluid are well known in the art, certain constituents in off-gas of the present invention cause excessive amounts of erosion and corrosion for many materials of construction when used in a turboexpander operating too near to the dewpoint of off-gas. Corrosive constituents are believed to comprise carboxylic acids and/or bromine in conjunction with water and/or dioxygen.

Accordingly, it is preferred to operate with the temperature at the outlet from at least one stage of a turboexpander of at least about 5, or 10, or 20, or 25° C. above the local dewpoint temperature of the off-gas. More preferably, these temperature clearances from dewpoint are maintained at the outlet from all stages of a turboexpander. Such temperatures are attained by various means comprising limiting the mechanical efficiency of a turboexpander, adding thermal energy to the off-gas between the exit from a solvent recovery and/or dehydration means and the exit of a turboexpander, and/or limiting the pressure reduction through a turboexpander.

However, once the dewpoint is sufficiently avoided, the inventors have discovered that it is often undesirable with respect to capital cost and operating cost to operate the current invention with too much superheat in turboexpander off-gas. Accordingly, it is preferred to operate with the temperature at the outlet of at least one stage of a turboexpander and at and off-gas condenser inlet of less than about 150, or 120, or 90, or 60° C. above the local dewpoint.

A less efficient turboexpander requires less added thermal energy to ensure that the turboexpander outlet temperature stays in a preferred dewpoint range. When less enthalpy is removed from the working fluid and converted to mechanical power, the exiting temperature from the turboexpander is inherently hotter. Depending on the relative costs of thermal heat and the costs for electrical power, improving mechanical efficiency of the turbine may be detrimental or beneficial for optimized cost. The inventors have discovered that when the unit cost of delivered thermal energy is less than about 0.3 times the cost of electrical power expressed in the same units, then it is preferred to maximize the mechanical efficiency of the turboexpander and to use additional thermal energy input to obtain the desired dewpoint range on the expander outlet. This is less efficiency than an electrical generating power cycle may achieve, e.g., at least about 0.5 ratio of mechanical energy output to thermal energy input, so the use of thermal energy input to the off-gas might seem ill-advised compared to the shaft work achieved. However, the dewpoint avoidance issue means that the incremental thermal energy input can be coupled with improved efficiency in the expander and/or increased decompression therein to achieve a remarkable overall improvement in energy recovery. Thus, it is preferred that the mechanical efficiency of a turboexpander employed in the present invention is at least about 65, or 75, or 80, or 85 percent of the maximum shaft work output possible to achieve by an ideal, isentropic expansion of the off-gas working fluid.

In order to increase mechanical power output from a turboexpander, especially in respect of maintaining the outlet temperature in a preferred range relative to the dewpoint while using a high efficiency turboexpander, it is preferred to provide the following amounts of thermal energy into off-gas between exiting a solvent recovery and/or dehydration means and a entering a turboexpander and/or at an interstage position in a multi-stage turboexpander: at least about 100, or 200, or 300, or 350 watts per kilogram of pX fed to corresponding oxidation reaction medium; less than about 1,000, or 800, or 600, or 500 watts per kilogram of pX fed to corresponding oxidation reaction medium; at least about 10, or 20, or 30, or 40 watts per kilogram of turboexpander off-gas; less than about 100, or 90, or 80, or 70 watts per kilogram of turboexpander off-gas; off-gas temperature rise from thermal energy input at least about 10, or 20, or 40, or 60° C.; and off-gas temperature rise from thermal energy input less than about 250, or 200, or 150, or 100° C.

Such amounts of thermal energy are supplied via heat exchange means comprising conductive, isolating, heat-exchange boundary surfaces, preferably comprising various corrosion resistant metals and metal alloys as known in the art. Preferably the thermal energy is supplied by a hot working fluid, more preferably steam condensing to form a portion of liquid water condensate. Furthermore, the inventors disclose that it is preferred to form at least a portion of lower pressure flash steam from condensate formed in an off-gas heat exchange means and to use at least a portion of said flash steam in at least one heat exchange means elsewhere in a TPA production process, e.g., heating a portion of xylene, recovered solvent, filtrate solvent, TPA solid, and/or off-gas.

Optionally, such amounts of thermal energy are supplied by oxidizing a fuel with dioxygen and directly combining the resulting hot reaction products into off-gas. Said hot reaction products are admitted at a location between exiting a solvent recovery and/or dehydration means and entering a turboexpander and/or at an interstage position in a multi-stage turboexpander. Preferably said fuel comprises hydrocarbyl bonds. More preferably, said fuel comprises an alcohol, acetate, and/or hydrocarbon. Still more preferably, said fuel predominantly comprises methanol, ethanol, methane, propane, butane, and/or fuel oil. Most preferably said fuel comprises at least about 50, or 70, or 90, or 95 weight percent methane.

Preferably a portion of compressed ambient air is provided for oxidizing said fuel, since off-gas from a solvent recovery and/or dehydration means is often relatively lean in dioxygen and rich in water vapor. More preferably at least about 50, or 70, or 90, or 100 weight percent of the stoichiometric amount of dioxygen is provided from compressed ambient air fed to an oxidation reaction zone for said fuel. The stoichiometric amount of dioxygen is the minimum amount required for full conversion of supplied fuel into water and carbon dioxide. Still more preferably less than least about 300, or 200, or 150, or 120 weight percent of the stoichiometric amount of dioxygen is provided from compressed ambient air fed to an oxidation reaction zone for said fuel. Preferably, the peak temperature for oxidizing said fuel is at least about 300, or 400, or 600, or 800° C. Preferably, an oxidation catalyst is not used to promote the oxidizing of at least about 10, or 50, or 80, or 95 weight percent of said fuel. Preferably, at least about 10, or 50, or 80, or 95 weight percent of the VOC in off-gas exiting a solvent recovery and/or dehydration means is not combusted before exiting the last stage of a turboexpander.

Besides increasing temperature and pressure at an inlet to a turboexpander, the inventors have discovered that the disclosures herein are also preferred for increasing the mass of water vapor reaching the inlet of at least one turboexpander means. These compositions are enabled by the disclosures herein pertaining to design and operation of a primary oxidation reaction medium, of a solvent recovery and/or dehydration means, and of connecting conduits. It is preferred that the composition of off-gas flowing into at least one turboexpander step comprises at least about 3.0, or 3.3, or 3.5, or 3.6 kilogram of water per kilogram of pX fed to corresponding oxidation reaction medium. It is preferred that the composition of off-gas flowing into at least one turboexpander step comprises at least about 0.38, or 0.42, or 0.44, or 0.46 kilogram of water per kilogram of off-gas at the same location. It is preferred that the mass flow of off-gas into the inlet of at least one turboexpander step is at least about 6.9, or 7.3, or 7.6, or 7.8 kilogram per kilogram of pX fed to corresponding oxidation reaction medium.

Attention is now returned to a solvent recovery and/or dehydration means. It is generally desirable to maximize the recovery from reaction off-gas of vaporized compounds containing at least one hydrocarbyl bond, herein called "volatile organic compounds" and "VOC". If not recovered from off-gas, these compounds are undesirably released to ambient surroundings or, more preferably, mostly converted to water vapor and carbon dioxide in a TOD. Although the TOD effluent is more environmentally benign, the loss of VOC from a solvent recovery and/or dehydration means remains an operating cost.

More specifically, it is generally desirable to limit the losses of pX, acetic acid, and methyl acetate in off-gas entering a TOD. Such loss minimization is influenced by various mechanical methods in a solvent recovery and/or dehydration means, but the separation is ultimately controlled by thermodynamics and by the energy expenditure in the solvent recovery and/or dehydration means. Generally, greater expenditures of energy may provide lower losses of VOC. Such energy expenditures result in lower temperatures and/or higher reflux ratios in a solvent recovery and/or dehydration means.

However, the inventors have discovered that intentionally increasing losses of volatile organic compounds above their bare minimum results in improved overall process economies when integrated with the fuel needs of a TOD and the shaft power recovery of a turboexpander.

Accordingly, it is preferred to control the energy removal and energy losses in at least one solvent recovery and/or dehydration means processing reaction off-gas as disclosed herein. It is preferred that the temperature of at least about 40, or 60, or 80, or 90 weight percent of off-gas exiting from a solvent recovery and/or dehydration means is less than about 50, or 40, or 30, or 25° C. reduced evaluated from where reaction off-gas is formed near an upper surface of reaction medium. It is preferred to insulate at least about 70, or 90, or 95, or 99 percent of the exposed, ambient surface area of conduits, vessels and controls comprising a solvent recovery and/or dehydration means with at least about 0.01, or 0.02, or 0.04, or 0.08 meters thickness of insulation material, despite that vast amounts of thermal energy are eventually released to ambient surroundings after a turboexpander. It is preferred that thermal energy losses through exposed, ambient surface area of conduits and/or vessels comprising a solvent recovery and/or dehydration means are less than about 40, or 20, or 10, or 5 watts per kilogram of pX fed to corresponding oxidation reaction medium.

It is preferred to limit thermal energy recovery such that less than about 1,000, or 100, or 1, or 0.1 watts of thermal energy per kilogram of pX fed to corresponding oxidation reaction medium is removed from process fluids through conductive, isolating, heat-exchange boundary surfaces located from where reaction off-gas is formed near an upper surface of reaction medium and until at least about 80, or 90, or 95, or 99 weight percent of the dinitrogen therein has passed through a turboexpanders means. Some designs known for recovery of energy from reaction off-gas comprise condensing and recovering solvent by extracting thermal energy across conductive, isolating, heat-exchange boundary surfaces to heat and/or vaporize utility fluids prior to off-gas passing through a turboexpander. The utility fluids are then used for generation of shaft power and/or transfer of thermal energy in other steps. Exemplary utility heat transfer and/or cooling fluids comprise water liquid and/or vapor, light aliphatic hydrocarbon liquid and/or vapor, and/or air.

It is preferred that a solvent recovery and/or dehydration means operates without adding an azeotropic separation compound. Exemplary azeotropic distillation compounds comprise n-butyl acetate and/or n-propyl acetate. It is preferred that a solvent recovery and/or dehydration means operates with net addition of less than about 0.1, or 0.01, or 0.001, or 0.0001 kilogram of azeotropic distillation compounds per kilogram of solvent recovered from reaction off-gas.

It is preferred that a solvent recovery and/or dehydration means of the present invention comprises a high efficiency distillation means processing at least about 80, or 90, or 95, or 99 weight percent of the non-condensable gases and/or dinitrogen present in reaction off-gas. It is preferred that said distillation means comprises at least about 20, or 25, or 30, or 35 ideal stages of separation. It is preferred that the flowing frictional pressure loss of off-gas through said distillation means is less than about 60, or 40, or 20, or 10 kilopascal. It is preferred that any distillation trays are of a low pressure drop design of less than about 1,200, or 900, or 700, or 500 Pascal per tray, notwithstanding that this undesirably limits the operating turndown of such trays. It is more preferred to use structured packing as is known in the art, notwithstanding the need for expensive, corrosion resistant metallurgy and also the potential flammability of some metals comprising titanium. It is preferred to construct said distillation means using at least two different vessel diameters wherein the maximum horizontal diameter of an upper section is less than about 1.0, or 0.96, or 0.92, or 0.90 times the maximum horizontal diameter that is present through at least about 4 meters of height in a lower section and is processing at least about 80, or 90, or 95, or 99 weight percent of the dinitrogen in reaction off-gas.

After exiting a turboexpander, it is preferred that at least a portion of off-gas gas is cooled in at least one heat exchange means, herein called an off-gas condenser, thereby producing a liquid, herein called reflux and essentially comprising water, at least a portion of which is fed into said solvent recovery and/or dehydration means. It is preferred that the various preferred ranges for temperature, pressure, and/or composition at the inlet of an off-gas condenser are the same as at an outlet of a final stage of a turboexpander. It is preferred that the flowing frictional pressure loss of off-gas is less than about 16, or 12, or 8, or 4 kilopascals in said off-gas condenser. When operating without an off-gas recompression step, it is preferred that the off-gas pressure exiting said off-gas condenser is at least about 0.02, or 0.08, or 0.12, or 0.16 bar gauge. When operating without an off-gas recompression step, it is preferred that the off-gas pressure exiting said off-gas condenser is less than about 0.6, or 0.5, or 0.4, or 0.3 bar gauge. When operating with an optional off-gas recompression step, it is preferred that the off-gas pressure exiting said off-gas condenser is at least about −0.8, or −0.7, or −0.6, or −0.5 bar gauge. When operating with an optional off-gas recompression step, it is preferred that the off-gas pressure exiting said off-gas condenser is less than about 0.1, or 0.0, or −0.1, or −0.2 bar gauge. It is preferred that the off-gas temperature exiting said off-gas condenser is at least about 30, or 40, or 50, or 60° C. It is preferred that the off-gas temperature exiting said off-gas condenser is less than about 110, or 100, or 90, or 80° C. It is preferred that the off-gas temperature exiting said off-gas condenser is reduced at least about 10, or 20, or 30, or 35° C. below turboexpander outlet temperature. It is preferred that the off-gas temperature exiting said off-gas condenser is reduced less than about 100, or 80, or 70, or 60° C. below turboexpander outlet temperature. It is preferred that thermal energy of less than about 3,100, or 2,900, or 2,700, or 2,500 watts is removed in said off-gas condenser per kilogram of pX fed to corresponding oxidation reaction medium. It is preferred that thermal energy of at least about 1,600, or 1,800, or 2,000, or 2,100 watts is removed in said off-gas condenser per kilogram of pX fed to corresponding oxidation reaction medium.

Reflux amount and temperature are selected and controlled to maximize the water vapor entering a turboexpander in balance with minimizing the loss of VOC in the off-gas exiting the condenser. It is preferred that the flow of reflux to a solvent recovery and/or dehydration means comprises at least about 7.0, or 8.0, or 8.5, or 9.0 kilogram of liquid water per kilogram of water of TPA formation produced in oxidation reactors served by said solvent recovery and/or dehydration means. It is preferred that the flow of reflux to a solvent recovery and/or dehydration means comprises less than about 12.0, or 11.0, or 10.5, or 10.0 kilogram of liquid water per kilogram of water of TPA formation produced in oxidation reactors served by said solvent recovery and/or dehydration means. It is preferred that the flow of reflux to a solvent recovery and/or dehydration means comprises at least about 0.70, or 0.75, or 0.79, or 0.82 kilogram of liquid water per kilogram of water vapor exiting from a solvent recovery and/or dehydration means. It is preferred that the flow of reflux to a solvent recovery and/or dehydration means comprises less than about 0.98*, or 0.96, or 0.92, or 0.90 kilogram of liquid water per kilogram of water vapor exiting from solvent recovery and/or dehydration means. (*When operating with optional direct firing of fuel, more water mass is formed by combustion of fuel.) It is preferred that the temperature of reflux fed to a solvent recovery and/or dehydration means is at least about 40, or 50, or 55, or 60° C. It is preferred that the temperature of reflux fed to a solvent recovery and/or dehydration means is cooled less than 40, or 30, or 20, or 10° C. below temperature of water vapor leaving condenser in off-gas.

The inventors note that placing an off-gas condenser at such low pressure according to the present invention greatly increases the volume of off-gas at a condenser entry and exit. Unless conduits of unusually large diameter are used, flowing velocities and frictional pressure drop are offensive. Accordingly, it is preferred that off-gas conduits between a turboexpander outlet and an off-gas condenser inlet have diameters of at least about 1.2, or 1.5, or 1.8, or 2.1 meters, which are quite large for pressure-containing process conduits made of various expensive, corrosion resistant metals and metal alloys. To mitigate the conduit diameter and cost, it is preferred that the superficial velocity of off-gas in conduits between a turboexpander outlet and an off-gas condenser inlet is at least about 30, or 40, or 50, or 60 meters per second. These are unusually fast conduit velocities re erosion, especially for a corrosive process gas near its dew point, and careful control is required versus the dewpoint. At the outlet of an off-gas condenser, the certain presence of liquid droplets increases the potential for erosion and corrosion, and it is preferred to limit superficial velocities in these conduits to less than about 30, or 25, or 20, or 15 meters per second until entering a knock-out means for liquid removal, as is disclosed elsewhere herein.

The inventors also note that operating an off-gas condenser at low pressure according to the present invention forces use of a lower process temperature in order to condense the required amount of reflux. The lower process temperature pinches closer to the temperature of the cooling fluid, and the lower process pressure causes a reduced film coefficient of heat transfer on the process side. All factors force an increased area of conductive, isolating, heat-exchange boundary surfaces, which typically comprise various expensive, corrosion resistant metals and metal alloys.

The design challenges and costs for an off-gas condenser of the present invention are still further amplified when expelling preferred amounts of water vapor to ambient surroundings according to some aspects of the present invention. Expelling selected amounts of water vapor introduces a requirement to control intentionally the amount of energy removed in an off-gas condenser even when operating with new or un-fouled conductive, isolating, heat-exchange boundary surfaces, with lower mass flow throughputs and/or energy duties when producing TPA at reduced production rates, and with variable temperatures of cooling medium as is often the case, e.g., due to diurnal and seasonal ambient changes.

A particular challenge for control of an off-gas condenser means is that most cooling tower water systems contain amounts of dissolved solids that are greatly concentrated by evaporative cooling with ambient air. When the flow of such cooling water is throttled to control the process temperature of an off-gas condenser, the temperature of exiting cooling water rises. If temperature of such cooling water rises too far, some of the dissolved solids precipitate. Unfortunately, many highly corrosion resistant metal alloys are rapidly attacked and perforated by pitting corrosion under such tuberculated deposits. Accordingly, the inventors disclose the following preferred embodiments for an off-gas condenser according to the present invention. As used herein, "condenser off-gas" comprises off-gas wherein at least a portion has been processed in at least one off-gas condenser.

It is preferred that said off-gas condenser producing liquid water comprises air-cooling wherein ambient air is in contact with conductive, isolating, heat-exchange boundary surfaces containing said off-gas. It is preferred that forced draft fans are used to move air flow across the conductive, isolating, heat-exchange boundary surfaces containing said off-gas. It is preferred that fan speed, fan blade pitch, air flow control louvers, and/or other air flow and/or air temperature control means are used to adjust the amount of off-gas cooling in response to at least one process variable; e.g., temperature and/or pressure of condenser off-gas; temperature and/or flow rate of condenser liquid; chemical composition of either condenser off-gas and/or condensate by any on-line measurement, e.g., infrared compositional analysis.

It is more preferred that said off-gas condenser producing liquid water comprises cooling water in contact with conductive, isolating, heat-exchange boundary surfaces containing said off-gas. It is preferred that cooling water flow rate, cooling water inlet temperature, and/or cooling water outlet temperature are used to adjust the amount of off-gas cooling in response to at least one process variable e.g., temperature and/or pressure of condenser off-gas; temperature and/or flow rate of condenser liquid; chemical composition of either condenser off-gas and/or condensate by any on-line measurement, e.g., infrared compositional analysis. It is preferred that at least a portion of cooling water exiting said water-cooled heat exchange means has a temperature of at least about 50, or 60, or 70, or 80° C. It is preferred that said cooling water comprises water cooled by direct contact with ambient air. It is more preferred that said cooling water is "enclosed loop cooling water". It is preferred that said enclosed loop cooling water comprises a reduced amount of Total Dissolved Solids (TDS), e.g., de-ionized water or steam condensate. It is preferred that at least a portion of heat is removed from said enclosed loop cooling water in a heat exchange means comprising utility cooling water cooled by direct contact with ambient air. It is preferred that at least a portion of heat is removed from said enclosed loop cooling water in a plate-and-frame heat exchange means.

Optionally, it is preferred that at least a portion of the conductive, isolating, heat-exchange boundary surface is removed from duty from time to time in response to at least one process variable e.g., temperature and/or pressure of condenser off-gas; temperature and/or flow rate of condenser liquid; chemical composition of either condenser off-gas and/or condensate by any on-line measurement, e.g., infrared compositional analysis. Said surface portion is removed from duty by removing it from contact with flowing off-gas and/or flowing utility cooling fluid.

An optional way for controlling the amount of energy removed in an off-gas condenser is to bypass a portion of turboexpander off-gas around said condenser, as is disclosed in U.S. Pat. No. 6,504,051, the entire disclosure of which is incorporated herein by reference. However, such gas bypassing creates new problems even while solving the need to adjust and control energy removal. Firstly, such bypassing intimately affects the mass balance as well as the energy balance because solvent vapor is not easily condensed from bypassed off-gas. If too much or too little gas is bypassed, while seeking to satisfy the energy balance, the water balance is upset for the solvent recovery system, making the recovered solvent become too wet or too dry; and there is also an upset in the amount of VOC sent toward ambient release and/or a TOD. Secondly, it is desirable to recombine condenser off-gas and bypassed off-gas for treatment in a shared, common environmental treatment means. However, such recombination is problematic because an aerosol fog is typically created when a colder, liquid-saturated gas flow is combined with a warmer, liquid-saturated gas. Such an aerosol proves dangerous with respect to pitting corrosion in conduits and equipment, for the aerosol is prone to collect as droplets on cooler and/or less turbulent surfaces. Rapid removal of such an aerosol from a high velocity process flow is difficult to achieve while limiting pressure drop and/or input of thermal energy, notwithstanding that such a fog may readily coalesce to rain liquid droplets when provided longer separation times.

Accordingly, the inventors have discovered the following preferred embodiments for the present invention. After exiting a turboexpander, at least a portion of off-gas gas is bypassed around at least one off-gas condenser to form a "bypassed off-gas" using one or more of the following preferred aspects. It is preferred that said bypassed off-gas is cooled less than about 60, or 50, or 30, or 10° C. in a heat exchange means comprising conductive, isolating, heat-exchange boundary surfaces before combining with off-gas exiting an off-gas condenser, entering a TOD, and/or being released to ambient surroundings. It is preferred that said bypassed off-gas is at least about 1, or 2, or 4, or 8 weight percent of all off-gas exiting a turboexpander. It is preferred that said bypassed off-gas is less than about 50, or 40, or 30, or 20 weight percent of all off-gas exiting a turboexpander. It is preferred that the flow rate of said bypassed off-gas is used to adjust the amount of off-gas cooling in response to at least one process variable; e.g., temperature and/or pressure of condenser off-gas; temperature and/or flow rate of condenser liquid; chemical composition of either condenser off-gas an/or condensate by any on-line measurement, e.g., infrared compositional analysis. It is preferred that said bypassed off-gas is combined with at least a portion of off-gas that has exited an off-gas condenser to form a "mixed off-gas" before release to ambient surroundings. It is preferred that a "knock-out means" utilizing at least one of the following features processes at least a portion of condenser off-gas, thereby producing a "knock-out off-gas". Preferably, at least about 10, 50, 98, 99.9 weight percent of the liquid entering said knock-out means is separated and exits commingled with less than about 50, or 95, or 99, or 99.8 weight percent of off-gas dinitrogen from an opening in the lower 80, or 60, or 40, or 10 percent of the height of said knock-out means. Preferably, at least a portion of said knock-out means is located at a lower elevation than at least one off-gas condenser providing gas-plus-liquid multiphase flow into said knock-out means. Preferably, liquid water exits said knock-out means from an opening located below a flow inlet from an off-gas condenser. Preferably, the superficial vertical velocity of off-gas in said knock-out means is less than about 4, or 3, or 2, or 1 meter per second at the plane of greatest horizontal diameter. Preferably, the superficial horizontal velocity of off-gas in said knock-out means is less than about 6, or 5, or 4, or 3 meters per second at the plane of greatest vertical diameter. Preferably, the mean residence time of off-gas in said knock-out means is less than about 20, or 13, or 8, or 5 seconds. Preferably, the mean residence time of off-gas in said knock-out means is at least about 0.5, or 1.0, or 1.5, or 2.0 seconds. Preferably, the mean residence time of liquid within said knock-out means is at least about 0.5, or 2, or 4, or 8 minutes. Preferably, the mean residence time of liquid within said knock-out means is less than about 60, or 48, or 24, or 12 minutes. Preferably, at least one liquid-removing impingement surface, other than pressure isolating boundary surfaces, is included within said knock-out means. Preferably, the solid surface area in contact with off-gas passing through a knock-out means is at least about 0.0005, or 0.001, or 0.002, or 0.004 square meters per kilogram of off-gas exiting said knock-out means. Preferably, at least a portion of off-gas passing through said knock-out means contacts at least about 0.001, or 0.005, or 0.01, or 0.02 square meters of non-pressure isolating solid surface area per kilogram of pX fed to corresponding oxidation reaction medium. Preferably at least about 70, or 80, or 90 percent of liquid droplets smaller than at least about 500, or 200, or 75, or 25 microns present in off-gas entering a knock-out means are removed from knock-out off-gas. The inventors disclose that these various preferred features for a knock-out means are preferred in a knock-out means processing condenser off-gas either with or without bypassed off-gas.

It is preferred that at least a portion of bypassed off-gas is processed in a TOD that also processes at least a portion of off-gas that has exited an off-gas condenser. More preferably, at least a portion of bypassed off-gas is combined with least a portion of condenser off-gas to form a mixed off-gas before entering a TOD. Most preferably, thermal energy is added to raise the temperature of said mixed off-gas before entering a TOD means. This heating reduces condensation in off-gas conduits, vessels and other enclosures and thus minimizes the cost for materials of construction. This thermal energy can be added in whole or part to said mixed off-gas flow, to said bypassed off-gas flow, or to said condenser exit off-gas flow. It is preferred that the temperature of said mixed off-gas is at least about 10, or 20, or 40, or 60° C. above the temperature of the off-gas exiting said off-gas condenser.

The inventors disclose that it is preferred to add thermal energy to knock-out off-gas according to this aspect even without bypassed off-gas. It is preferred to locate the off-gas condenser and the knock-out means as follows, in order to balance simultaneously the cost of pumping cooling water to high elevations, the cost for tall structures and supports, and the provision of elevation to enable gravity flow of condensed liquid in and/or through an off-gas condenser and/or knock-out means. It is preferred that the elevation of a lowest cooled surface in at least one off-gas condenser is less than about 50, or 30, or 20, or 10 meters above ground surface elevation. It is preferred that the elevation of a highest cooled surface in at least one off-gas condenser is at least about 6, or 9, or 12, or 15 meters above ground surface elevation. It is preferred that the elevation of a liquid inventory within a knock-out means is at least about 0.5, or 1, or 2, or 3 meters above the surface elevation of surround ground. It is preferred that the elevation of a liquid inventory within a knock-out means is less than about 20, or 15, or 10, or 5 meters above ground surface elevation.

In combination with improved power recovery from an off-gas turboexpander and/or self-heating of a TOD according to disclosures herein, the inventors have discovered a surprising benefit from leaving increased amounts of water vapor in vented off-gas, notwithstanding the greater losses of VOC that often accompany such increased amounts of water vapor. Accordingly the inventors disclose the following preferred embodiments for "vented water vapor" present in a condenser off-gas, a knock-out off-gas, and/or a TOD inlet off-gas. It is preferred that the vented water vapor is less than about 400, or 300, or 250, or 200 weight percent of the water of TPA formation. This avoids expending too much heat of oxidation reaction in vaporizing water liquid in a once through turboexpander power cycle with subsequent capital and operating costs for treatment in a TOD and without a concomitant increase in supply of reflux for a solvent recovery and/or dehydration means. It is preferred that the vented water vapor is at least about 100, or 110, or 130, or 150 weight percent of the water of TPA formation. To avoid overly dehydrating the recovered solvent system and thereby upsetting the oxidation reaction conditions, preferred sources of the water amount exceeding the water of TPA formation are disclosed herein.

It is preferred that vented water vapor in excess of the water of TPA formation comprises at least a portion of water that has entered the process with the oxidant supply, more preferably compressed ambient air. The preferred amount of water vapor entering in compressed air is disclosed elsewhere herein. It is preferred that vented water vapor in excess of the water of TPA formation comprises at least a portion of water formed from over-oxidation of aromatics and solvent. It is preferred that vented water vapor comprises at least about 0.05, or 0.10, or 0.15 kilogram of water formed from over-oxidation of aromatics and solvent per kilogram of pX fed to corresponding oxidation reaction medium. It is preferred that vented water vapor comprises less than about 0.05, or 0.04, or 0.03 kilogram of water formed from over-oxidation of aromatics and solvent per kilogram of pX fed to corresponding oxidation reaction medium.

It is preferred that vented water vapor in excess of the water of TPA formation comprises water formed from injection of pressurized steam (at least about 50, 90, 95, 99 weight percent water, at least about 110, or 140, or 180, or 220° C.) into a process flow comprising liquid solvent. Preferred applications comprise steam as a source of thermal energy and as a flushing medium for conduits, orifices, and equipment. It is preferred that vented water vapor in excess of the water of TPA formation comprises at least a portion of water used to scrub process vents that subsequently release gas to ambient surroundings. It is preferred that vented water vapor in excess of the water of TPA formation comprises at least a portion of water used as an azeotropic separation aid in a solvent purification and/or catalyst recovery process comprising disclosures in U.S. Pat. No. 4,939,297, U.S. Pat. No. 7,351,396, and U.S. Pat. App. Pub. No. 2005-0038288.

It is preferred that vented water vapor in excess of the water of TPA formation comprises at least a portion of water formed from oxidation of fuel when optionally used to heat off-gas between an outlet from a solvent recovery and/or dehydration means and an outlet from a turboexpander.

It is preferred that vented water vapor in excess of the water of TPA formation comprises at least a portion of water coming from an adjacent PET process and entering the TPA process before the outlet of a TOD, more preferably before the inlet of a TOD. It is preferred that said PET process is located such that the minimum horizontal distance from said TPA process is less than about 1800, 900, 300, 100 meters. It is preferred that said PET process forms at least a portion of PET using TPA product from said TPA process. It is preferred that at least a portion of said TPA product is fed into a reaction medium of said adjacent PET process within less than about 72, or 24, or 12, or 4 hours after being formed from para-xylene, para-tolualdehyde and/or para-toluic acid. It is preferred that the water coming from said PET process is at least about 0.02, or 0.2, or 0.3, or 0.4 kilogram per kilogram of water of formation of TPA. It is preferred that the water coming from said PET process is less than about 1.1, or 0.9, or 0.7, or 0.6 kilogram per kilogram of water of formation of TPA.

It is preferred that a TOD is self-fueled by oxidation of off-gas compounds comprising carbon monoxide and VOC, especially by oxidation of methyl acetate. It is preferred that the fuel content of off-gas is at least about 60, 70, 80, 90 percent of all fuel content entering TOD. Fuel content is evaluated as the heat of oxidation reactions yielding vapor phase products comprising water vapor and carbon dioxide gas. It is preferred that fuel content of off-gas is less than about 160, or 140, or 120, or 110 percent of the minimum fuel content needed to operate the TOD without a cooling means, e.g., sensible heating of air or other gas/vapor and/or sensible or latent heating of water or other liquid, whether directly by commingling mass or indirectly across isolating conductive heat exchange surfaces.

It is preferred that a TOD is usefully, even predominantly, fueled by methyl acetate in off-gas according to the following disclosures. Methyl acetate is a known byproduct of the liquid-phase oxidation of pX to TPA in acetic acid. Technologies are known in the art for isolating methyl acetate and then hydrolyzing it with water to recover acetic acid solvent and byproduct methanol effluent. The inventors have discovered that an efficient TPA synthesis system, e.g., US 20070293699 and US 20070208191 (the entire disclosures of which are incorporated by reference herein), provides a useful reduction in the net formation rate of methyl acetate. The CO component in off-gas has a relatively low heating value, and off-gas often contains relatively small amounts of MeBr and acetic acid. Methyl acetate provides useful fuel content to a TOD in order to achieve required temperatures and destruction efficiencies of pollutants, including methyl acetate itself. If the fuel content of off-gas is too low, then supplementary fuels, e.g., methane, methanol, fuel oil, must be supplied to the TOD in order achieve required temperatures and destruction efficiencies of pollutants.

The inventors have discovered the following preferred ranges for methyl acetate in knock-out off-gas, ranges that usefully balance the fuel value of methyl acetate in a TOD against the capital and operating costs for further suppression of formation of methyl acetate and/or recovery of its acetic acid content by separation and hydrolysis. It is preferred that methyl acetate content in knock-out off-gas and/or off-gas entering a TOD is at least about 0.003, or 0.005, or 0.007, or 0.008 kilogram per kilogram of pX fed to corresponding oxidation reaction medium. It is preferred that methyl acetate content in knock-out off-gas and/or off-gas entering a TOD is less than about 0.030, or 0.025, or 0.020, or 0.015 kilogram per kilogram of pX fed to corresponding oxidation reaction medium. It is preferred that methyl acetate provides at least about 20, or 30, or 40, or 50 percent of all fuel content entering a TOD. In another embodiment of the invention, it is preferred that methyl acetate and/or methanol content in knock-out off-gas and/or off-gas entering a TOD is less than about 0.030, or 0.025, or 0.020, or 0.015 kilogram per kilogram of pX fed to corresponding oxidation reaction medium. It is preferred that methyl acetate provides at least about 20, or 30, or 40, or 50 percent of all fuel content entering a TOD.

It is preferred that acetic acid content in knock-out off-gas and/or off-gas entering a TOD is less than about 0.005, or 0.004, or 0.003, or 0.002 kilogram per kilogram of pX fed to corresponding oxidation reaction medium. It is preferred that carbon monoxide content in knock-out off-gas and/or off-gas entering a TOD is less than about 0.45, or 0.40, or 0.35, or 0.30 mole percent evaluated on a dry basis with only non-condensable gaseous compounds.

However, it is undesirable to waste too much energy, whether combustible fuel intrinsic in an off-gas or added fuel, in the TOD. Therefore, it is preferred that the total combustion energy released by a TOD is less than 600, or 500, or 450, or 400 kilojoules per kilogram of pX fed to corresponding oxidation reaction medium. This low amount of required combustion heat is achieved by providing efficient heat integration between hot, treated off-gas near the exit of a TOD and untreated off-gas near the entry to said TOD, as is known in the art by various means.

The supply of combustion heat is appropriately controlled with the operating methods and off-gas compositions as disclosed herein. It is preferred that a TOD operates with a peak internal temperature of at least about 200, or 400, or 600, or 800° C. It is preferred that at least about 94, or 96, or 98, or 99 mole percent of carbons in off-gas entering a TOD are oxidized to CO2 before exiting the TOD. Most preferably, the TOD means in all disclosures herein is a Regenerative Thermal Oxidation (RTO) means.

After removal and/or destruction of carbon monoxide and VOC pollutants in an oxidation reaction off-gas, many locales require substantial removal of bromine from the treated off-gas. This bromine reduction is often done by aqueous scrubbing of the treated off-gas from a TOD, e.g., liquid scrubbing of off-gas using an aqueous solution of sodium hydroxide and sodium bisulfite to produce sodium bromide salt. Over time the concentration of various salts builds up in scrubber water, and an effluent blowdown must be provided along with a makeup of purer water. Preferably, said off-gas scrubber makeup water is filtered water. More preferably, said scrubber makeup water is de-mineralized water, de-ionized water, and/or steam condensate.

The inventors have discovered that said scrubber liquid blowdown effluent essentially comprising water is advantageously used as utility water, e.g., cooling tower makeup water. Accordingly, it is preferred to use at least about 0.01, or 0.05 kilogram of off-gas scrubber liquid effluent water per kilogram of pX fed to corresponding oxidation reaction medium as utility water rather than discharging said scrubber water to a wastewater treatment unit and/or directly to ambient surroundings. In another embodiment of the invention any effluent water obtained from a production facility comprising an oxidation reaction medium can be used at a rate of 0.01 to 0.05 kilogram of effluent water per kilogram of pX fed corresponding oxidation reaction medium as utility water rather than discharging the utility water to a wastewater treatment unit and/or directly to ambient surroundings In an optional and more preferred embodiment, the invention comprises combining oxidation reaction off-gas, including both primary and secondary oxidation reactor sources, for processing through a shared combined solvent recovery and/or dehydration means, turboexpander means, condenser means, knock-out means, TOD and/or bromine scrubber.

Undesirably with respect to energy recovery, the operating pressures and temperatures of secondary reaction mediums are often substantially different, sometimes significantly higher, from a primary reaction medium and/or from each other. The simple expansion of higher pressure reaction off-gases across a pressure reduction valve into lower pressure off-gas usually dissipates significant entropy, causing a loss in subsequent ability to produce shaft work. However, the present invention usefully retains enthalpy in the combined off-gases at the inlet to a turboexpander, and the combined off-gas flows usefully commingle CO and VOC fuel values ahead of a TOD.

It is preferred to process off-gas from at least two distinct reaction mediums in a shared, common solvent recovery and/or dehydration means, turboexpander means, condenser means, knock-out means, TOD and/or bromine scrubber. It is preferred that at least portion of said distinct reaction mediums are separated horizontally from each other by less than about 1,000, or 500, or 300, or 150 meters. "Process integrated" means that feed or product streams from two different processes/facilities are combined and processed using at least one piece of common equipment selected from the group consisting of turboexpander means, condenser means, knock-out means, TOD and/or bromine scrubber.

When forming an off-gas mixture, it is preferred that the amount of all off-gas in the mixture that is sourced from secondary oxidation reaction medium is much less than the amount of all off-gas in the mixture that is sourced from primary oxidation reaction medium. In mixtures of primary and secondary off-gas, it is preferred that off-gas arising from secondary oxidation reaction mediums comprises less than about 20, or 10, or 5, or 2 weight percent of the mass of combined off-gas and less than about 20, or 10, or 5, or 2 weight percent of the mass of dinitrogen of combined off-gas. In mixtures of primary and secondary off-gas, it is preferred that off-gas arising from secondary oxidation reaction mediums comprises at least about 0.1, or 0.2, or 0.4, or 0.8 weight percent of the mass of combined of off-gas and less than about 0.1, or 0.2, or 0.4, or 0.8 weight percent of the mass of dinitrogen of combined off-gas.

It is preferred that at least about 40, or 60, or 80, or 90 weight percent of reaction off-gas from at least one secondary oxidation reaction medium is combined with at least about 40, or 60, or 80, or 90 weight percent of reaction off-gas from a primary oxidation reaction medium for processing in a shared, common solvent recovery and/or dehydration means, turboexpander means, condenser means, knock-out means, TOD, and/or bromine scrubber. It is preferred that at least a portion of off-gas from said secondary medium is formed at a temperature of at least about 160, or 175, or 190, or 200° C. It is preferred that at least a portion of off-gas from said secondary medium is formed at a temperature of less than about 250, or 240, or 230, or 220° C. It is preferred that at least a portion of off-gas from said secondary medium is formed at a pressure of at least about 7, or 10, or 13, or 16 bara. It is preferred that at least a portion of off-gas from said secondary medium is formed at a pressure of less than about 40, or 34, or 28, or 24 bara.

It is preferred that at least a portion of reaction off-gas from at least two distinct secondary oxidation reaction mediums are combined with each other and with at least a portion of reaction off-gas from a primary oxidation reaction medium for processing in a shared, common solvent recovery and/or dehydration means, turboexpander means, condenser means, knock-out means, TOD, and/or bromine scrubber. It is preferred that at least a portion of off-gas from at least one secondary medium is formed at a temperature of less than about 20, or 15, or 10, or 5° C. greater than a portion of said off-gas from said primary oxidation reaction medium. It is preferred that at least a portion of off-gas from one secondary medium is formed at a temperature of at least about 10, or 15, or 25, or 35° C. greater than a portion of said off-gas from said primary oxidation reaction medium and/or a portion of said off-gas from a distinct secondary oxidation reaction medium. It is preferred that at least a portion of said off-gas from one secondary medium is formed at a temperature of less than about 20, or 15, or 10, or 5° C. different than a portion of said off-gas from a distinct secondary oxidation reaction medium. It is preferred that at least one of said reaction off-gases comes from a secondary oxidation reaction medium separated horizontally from a portion of said primary reaction medium by less than about 60, or 20, or 8, or 2 meters. It is preferred that at least one of said reaction off-gases comes from a secondary oxidation reaction medium separated horizontally from a portion of said primary reaction medium by at least about 4, or 8, or 16, or 32 meters.

It is preferred to process at least about 40, or 60, or 80, or 90 weight percent of the dinitrogen in reaction off-gas from at least one secondary oxidation reaction medium combined with at least about 40, or 60, or 80, or 90 weight percent of the dinitrogen in reaction off-gas from a primary oxidation reaction medium in a shared, common turboexpander means, condenser means, knock-out means, TOD, and/or bromine scrubber.

The inventions herein are preferred for a process producing a crude TPA, in which total monocarboxylic acid impurities comprise at least about 1,000, or 2,000, or 4,000, or 6,000 ppmw; producing a purified TPA, in which total monocarboxylic acid impurities comprise less than about 1,000, or 500, or 300, or 200 ppmw; and producing both crude and purified TPA simultaneously in any relative ratio. Monocarboxylic acid impurities notably comprise benzoic acid, para-toluic acid, and 4-carboxybenzaldehyde.

The inventions herein are more preferred for producing purified TPA with a b* color of less than about 4.0, or 3.5, or 3.0, or 2.5 b* units. The b* value as used herein is one color attribute measured on a spectroscopic instrument such as a Hunter Ultrascan XE instrument (Hunter Associates Laboratory, Inc., 11491 Sunset Hills Road, Reston, Va. 20190-5280, www.hunterlab.com) using a reflectance mode. Positive readings signify the degree of yellow (or absorbance of blue), while negative readings signify the degree of blue (or absorbance of yellow).

The inventions herein apply for processes converting m-xylene (mX) into isophthalic acid (IPA) in all aspects of the disclosures by substituting the meta-species for the para-species, e.g., mX for pX, IPA for TPA, meta-toluic acid for para-toluic acid, and 3-carboxybenzaldehyde for 4-carboxybenzaldehyde. This extension applies for a process making IPA separately. The extension also applies in partially and/or fully combined processes making both TPA and IPA.

Aspects of the invention pertaining to combining reaction off-gas from different reaction mediums for processing in at least one solvent recovery and/or dehydration means, turboexpander, condenser, knock-out means, TOD, and/or bromine scrubber apply in all aspects also when the preponderant aromatic species in at least one reaction medium is para-substituted and the preponderant aromatic species in at least one other reaction medium is meta-substituted. All aspects of the invention pertaining to recovered solvent apply also when at least a portion of solvent recovered from reaction off-gas from oxidizing one xylene is subsequently used within 72, or 48, or 24, or 12 hours in reaction medium oxidizing the other xylene. All aspects of the invention pertaining to filtrate solvent apply also when at least a portion of filtrate solvent formed by separation from a solid product that is predominantly one aromatic dicarboxylic acid is subsequently used within 72, 48, 24, 12 hours in reaction medium oxidizing the other xylene. (Even though it is possible, and often preferable, to keep Co/Mn/Br even heavy aromatic impurities from one filtrate isolated from the other, it is not preferred to keep the water, acetic acid and benzoic acid components separated.)

It is preferred to treat at least a portion of filtrate solvent (para-filtrate) from a process wherein the preponderant aromatic species are para-substituted and a portion of filtrate solvent (meta-filtrate) from a process wherein the preponderant aromatic species are meta-substituted in a solvent purification and/or catalyst recovery process sharing at least one conduit, pressure containing vessel, and/or rotating equipment item. Suitable filtrate purification units are comprised disclosures in U.S. Pat. No. 4,939,297, U.S. Pat. No. 7,351,396, and U.S. Pat. App. Pub. No. 2005-0038288 (the entire disclosures of which are incorporated herein by reference). It is more preferred that at least a portion of para-filtrate and of meta-filtrate is co-fed at the same time, as compared to being campaigned in sequence. It is preferred that at least a portion of purified filtrate and/or at least a portion of recovered catalyst from said process are subsequently used to form at least a portion of oxidization reaction medium and subsequently to form a portion of para-filtrate or of meta-filtrate, more preferably forming a portion of both filtrates. It is preferred that at least about 10, or 40, or 80, or 98 weight percent of the aromatic impurities removed from para-filtrate by said filtrate solvent purification and/or catalyst recovery process are physically combined with at least about 10, or 40, or 80, or 98 weight percent of the aromatic impurities removed from meta-filtrate by said process.

All aspects of the invention pertaining to compressed air for oxidant supply apply when a portion of compressed air from a compression means is divided to provide oxidant supply to at least one oxidation reaction medium wherein the preponderant aromatic species are para-substituted and at least one other oxidation reaction medium wherein the preponderant aromatic species are meta-substituted.

All aspects of the invention pertaining to oxidant-supply-intercooler-condensate apply when at least a portion of oxidant-supply-intercooler-condensate is divided with part being used in at least one process step wherein the preponderant aromatic species are para-substituted and with another part being used in at least one other process step wherein the preponderant aromatic species are meta-substituted.

In one embodiment, it is preferred that that a smaller IPA manufacturing process is co-located with a larger TPA manufacturing process. When off-gas from at least one preponderantly meta-substituted reaction medium is combined with off-gas from at least one preponderantly para-substituted reaction medium, it is preferred that the off-gas arising from preponderantly meta-substituted medium comprises less than about 50, or 40, or 30, or 20 weight percent of the mass of combined off-gas and less than about 50, or 40, or 30, or 20 weight percent of the mass of dinitrogen in the combined off-gas.

When off-gas from at least one preponderantly meta-substituted reaction medium is combined with off-gas from at least one preponderantly para-substituted reaction medium, it is preferred that the off-gas arising from preponderantly meta-substituted mediums comprises at least about 0.5, or 1.0, or 1.5, or 2.0 weight percent of the mass of combined off-gas and less than about 0.5, or 1.0, or 1.5, or 2.0 weight percent of the mass of dinitrogen in the combined off-gas.

When an ambient air compression means supplies oxidant to at least one preponderantly meta-substituted reaction medium and to at least one preponderantly para-substituted reaction medium, it is preferred that preponderantly meta-substituted reaction mediums receive less than about 50, or 40, or 30, or 20 weight percent of the total mass flow of oxidant from said air compression means. When an ambient air compression means supplies oxidant to at least one preponderantly meta-substituted reaction medium and to at least one preponderantly para-substituted reaction medium, it is preferred that preponderantly meta-substituted reaction mediums receive at least about 0.5, or 1.0, or 1.5, or 2.0 weight percent of the total mass flow of oxidant from said air compression means.

It is more preferred that said IPA and TPA manufacturing processes are co-located with at least one co-located PET manufacturing process. It is preferred that IPA produced in said co-located process comprises at least about 0.5, or 1.0, or 1.5, or 2.0 weight percent of all dicarboxylic acid fed to a co-located PET manufacturing process. It is also preferred that IPA produced in said co-located process comprises less than about 16, or 12, or 8, or 4 weight percent of all dicarboxylic acid fed to a co-located PET manufacturing process.

In another embodiment, with or without co-locating IPA and TPA, it more preferred that at least a portion of IPA fed from a primary reaction medium comprising preponderantly meta-substituted species is fed to a PET reaction medium without said IPA having been purified by dissolving, selectively hydrotreated, and re-precipitating to remove 3-CBA and/or colored species.

In one embodiment, it is preferred that said IPA fed to PET reaction medium is either crude IPA directly from a primary oxidation reaction medium that is preponderantly meta-substituted or is post-oxidized IPA formed in a secondary reaction medium whose average reaction temperature is less than about 24, 16, 12, 8 degrees hotter than said primary reaction medium. It is preferred that said crude IPA and/or post oxidized IPA comprises at least about 20, or 80, or 160, or 320 ppmw of 3-CBA; less than about 3,000, or 2,400, or 1,800, or 1,200 ppmw of 3-CBA; at least about 2, or 4, or 8, or 16 ppmw of 2,6-DCF; and less than about 160, or 120, or 80, or 60 ppmw of 2,6-DCF.

In another embodiment, it is preferred that said IPA fed to PET is digested IPA formed in a secondary reaction medium whose average reaction temperature is at least about 16, or 24, or 30, or 36° C. hotter than said primary reaction medium and less than about 80, or 70, or 60, or 50° C. hotter than said primary reaction medium. It is preferred that said digested IPA comprises at least about 10, or 40, or 60, or 80 ppmw of 3-CBA; less than about 1,000, or 800, or 500, or 300 ppmw of 3-CBA; at least about 2, or 4, or 6, or 8 ppmw of 2,6-DCF; and less than about 120, or 80, or 60, or 40 ppmw of 2,6-DCF.

Another aspect of the present invention relates to improved disposition of ambient water condensed and removed, rather than being retained as vapor, during compression of ambient air for oxidant supply. Compression means for supplying pressurized ambient air often comprise multistage compression systems using at least one intercooler to remove heat of compression to make the process more thermodynamically and mechanically efficacious. Such systems typically produce condensed water in interstage coolers, and this water is typically separated from air before the inlet to a subsequent compression stage. Because such oxidant-supply-intercooler-condensate may be contaminated with lubricants and/or seal fluids, said condensate is conventionally directed to a wastewater treatment facility, perhaps only an oil skimmer though sometimes comprising biological or other treatment technologies.

The inventors have discovered the following improved uses for oxidant-supply-intercooler-condensate, simultaneously reducing wastewater treatment costs and reducing costs for purchasing and/or purifying utility water. It is preferred to feed at least a portion of oxidant-supply-intercooler-condensate into a TPA process and/or adjacent PET process, more preferably in at least one of following process steps. A TPA solvent recovery and/or dehydration means, especially as reflux as defined herein. A TPA filtrate solvent purification system, especially as an azeotropic separation aid for recovery or TPA catalyst components, more preferably comprising isopropyl acetate according to references contained herein. A process for purifying TPA by selective, catalytic hydrogenation of crude TPA. A scrubber on an ambient vent from either a TPA or PET process or storage vessel.

It is preferred to feed at least a portion of oxidant-supply-intercooler-condensate into at least one utility water system, more preferably comprising the following systems, and most preferably for use by a TPA process and/or adjacent PET process. A cooling water system, more preferably a cooling tower water system wherein water is cooled by direct contact with air. A filtered water system. A de-ionized and/or de-mineralized water system. A fire water system.

The amount of oxidant-supply-intercooler-condensate varies with ambient humidity, with cooling medium temperature, with pX feed rate, and with excess dioxygen in reaction off-gas, both transiently and on average. Accordingly, it is preferred that preferred, disclosed uses comprise at least about 0.01, or 0.02, or 0.04, or 0.08 kilogram of oxidant-supply-intercooler-condensate per kilogram of pX fed to corresponding oxidation reaction medium.

Generally, it is preferred to vent water vapor in approximately continuous balance with its introduction via various process steps; but nonetheless, it is inevitable that there are production upsets and maintenance activities that produce a temporary excess of liquid wastewater. For example, opening a process vessel for inspection or repairs during a process shutdown is often preceded by thoroughly water washing or steaming to remove essentially all solvent, substrate, and product; and the amount of such upset-water can be large for major maintenance activities. It is preferred to provide at least one storage reservoir for liquid wastewater and that this liquid wastewater is subsequently returned to at least one process step and subsequently vented as water vapor according to other disclosures herein. It is preferred that such liquid wastewater storage reservoirs provide effective isolation to control release of VOC to ambient surroundings. It is preferred that the volume of such storage reservoirs is at least about 50, or 100, or 200, or 400 cubic meters. It is preferred that the volume of such storage reservoirs is less than about 12,000, or 9,000, or 6,000, or 3,000 cubic meters.

By combining various aspects relating to expelling water in vapor form to ambient surroundings, more preferably after treatment in a TOD, along with using oxidant-supply-intercooler-condensate and/or bromine scrubber water in disclosed applications for process and/or utility water, it is preferred to produce less than about 400, or 350, or 300, or 250, or 200, or 100, or 50, or 20 gram of liquid wastewater effluent per kilogram of solid TPA product formed. It is preferred that this performance is maintained essentially continuously for long periods. It is preferred to produce these low levels of liquid wastewater effluent for at least about 60, or 80, or 90, or 95 percent of the time in a continuous 24 hour period. It is preferred to produce these low levels of liquid wastewater effluent averaged over a period of at least about 4, or 16, or 64, or 254 days. A PET synthesis facility also produces water from reactions converting at least a portion of TPA into PET, and this water is often contaminated with various VOC compounds, e.g., ethylene glycol, acetaldehyde, and various dioxolanes. It is preferred to treat at least a portion of contaminated water of PET formation in a shared, common facility along with water of TPA formation from an adjacent TPA facility. Preferably, said contaminated water from PET formation is left in vapor form exiting said PET facility for treatment, or it is converted to a vapor form using at least a portion of thermal energy from said adjacent TPA facility.

In another embodiment of the invention, the amount of water generated as a byproduct or added to oxidation that is exiting said production facility to the ambient external environment as a vapor is at least 0.3, or 0.4, or 0.49 kilograms per kilogram of aromatic compound. As used herein production facility can include wastewater treatment. More preferably, at least a portion of vaporized water of PET formation from reactions in an adjacent PET synthesis facility is treated along with at least a portion vaporized water of TPA formation in a shared, common TOD, still more preferably an RTO, according at any and/or all disclosures herein pertaining to the processing of reaction off-gas from oxidation reaction medium. It is preferred that at least a portion of oxidation reaction medium forming TPA is located such that the minimum horizontal distance from said PET synthesis facility is less than about 1800, or 900, or 300, or 100 meters. It is preferred that at least a portion of TPA is fed into a reaction medium of said adjacent PET synthesis facility within less than about 72, or 24, or 12, or 4 hours after being formed from para-xylene. It is preferred to process at least about 40, or 60, or 70, or 80 weight percent of the off-gas from said adjacent PET synthesis facility in a shared, common TOD, more preferably RTO, with at least about 40, or 60, or 70, or 80 weight percent of the reaction off-gas from at least one primary oxidation reaction medium. It is preferred to process at least about 40, or 60, or 70, or 80 weight percent of the water of TPA formation from a TPA production facility is processed in a shared, common TOD, more preferably RTO, with at least about 40, or 60, or 70, or 80 weight percent of the water of forming PET in said adjacent PET production facility.

It is preferred that the normal flow of process wastewater effluent from said adjacent PET production facility combined with the normal flow of process wastewater effluent from said TPA production facility is less than about 400, or 200, or 100, or 50 grams of liquid wastewater effluent per kilogram of PET formed. If the amount TPA produced in said TPA production facility differs from the amount of TPA consumed in said adjacent PET production facility by more than 10 weight percent, then the liquid wastewater effluent from said TPA facility is prorated by the ratio of its usage in said PET facility, this value is summed with the liquid wastewater effluent from said PET facility, and the is divided by the amount of PET produced.

We claim:

1. A process for making terephthalic acid and/or isophthalic acid, said process comprising:
   (a) oxidizing an aromatic compound in at least one oxidizer to thereby produce an oxidizer off-gas and an oxidizer slurry comprising terephthalic acid and/or isophthalic acid, wherein the at least one oxidizer comprises a bubble column reactor, and wherein the aromatic compound is at least one member selected from para-xylene and meta-xylene, wherein said oxidizer off-gas contains at least 12.4 kilograms of vapor per kilogram of said aromatic compound fed to said oxidizer; wherein said oxidizing is performed at a temperature of from 140 to 170° C. at a pressure of less than 8 bara;
   (b) recovering hydrocarbyl compounds from said oxidizer off-gas in a solvent recovery system to thereby produce a hydrocarbyl-depleted off-gas comprising at least 3 kilograms of water vapor per kilogram of said aromatic compound fed to said oxidizer; and
   (c) passing at least a portion of said hydrocarbyl-depleted off-gas through at least one turboexpander to thereby generate work, wherein said hydrocarbyl-depleted off-gas fed to said turboexpander comprises at least 3 kilograms of water vapor per kilogram of said aromatic compound fed to said oxidizer.

2. The process according to claim 1 wherein said oxidizer off-gas comprises at least 13.2 kilograms of vapor per kilogram of said aromatic compound fed to said oxidizer.

3. The process according to claim 1 wherein said oxidizer off-gas comprises vapor compounds including vaporized water and vaporized hydrocarbyl compounds.

4. The process according to claim 3 wherein said oxidizer off-gas comprises said vapor compounds in an amount of at least about 50 weight percent.

5. The process according to claim 1 wherein the mass of water vapor passed through said turboexpander is at least 50 percent of the amount of the mass of water exiting said solvent recovery system in said hydrocarbyl-depleted off-gas stream.

6. The process according to claim 5 wherein said hydrocarbyl-depleted off-gas is not subjected to thermal oxidative destruction (TOD) prior to entering said turboexpander.

7. The process according to claim 1 further comprising returning at least a portion of the recovered hydrocarbyl compounds to said oxidizer as recovered solvent.

8. The process according to claim 7 wherein at least 40 weight percent of said recovered solvent is supplied to said oxidizer at a temperature within 80° C. of the temperature of said oxidizer off-gas.

9. The process according to claim 1 further comprising subjecting a slurry comprising solid particles of said aromatic dicarboxylic acid and liquid solvent to solid-liquid separation and/or washing, further comprising recovering a filtrate solvent from said solid-liquid separation and/or washing step and returning at least a portion of said filtrate solvent to said oxidizer.

10. The process according to claim 9 wherein at least 40 weight percent of said filtrate solvent supplied to said oxidizer enters said oxidizer at a temperature of at least about 60° C.

11. The process according to claim 1 further comprising compressing air in an air compressor and feeding the resulting compressed air to said oxidizer.

12. The process according to claim 11 wherein said air compressor is at least partly powered by said turboexpander.

13. The process according to claim 12 wherein a turboexpander off-gas is discharged from said turboexpander, wherein the discharge pressure of said turboexpander off-gas is at least 0.05 barg and less than about 0.9 barg.

14. The process according to claim 1 wherein said hydrocarbyl-depleted off-gas fed to said at least one turboexpander comprises at least 3.3 kilograms of water vapor per kilogram of said aromatic compound fed to said oxidizer.

15. The process according to claim 1 wherein said hydrocarbyl-depleted off-gas fed to said at least one turboexpander comprises at least 40 mole percent water.

16. The process according to claim 15 further comprising removing at least about 10 weight percent of the water vapor present in said turboexpander off-gas as liquid water to thereby provided a condenser off-gas.

17. The process according to claim 16 wherein the discharge pressure of said turboexpander off-gas is at least −0.9 barg and less than about 0.3 barg.

18. The process according to claim 16 wherein said solvent recovery system does not employ an azeotropic distillation compound.

19. The process according to claim 1 wherein said aromatic compound is para-xylene.

20. A process for making terephthalic acid and/or isophthalic acid, said process comprising:
(a) oxidizing an aromatic compound in at least one oxidizer to thereby produce an oxidizer off-gas and an oxidizer slurry comprising an aromatic dicarboxylic acid, wherein the at least one oxidizer comprises a bubble column reactor, and wherein the aromatic compound is at least one member selected from para-xylene and meta-xylene, wherein said oxidizer off-gas contains at least 13.2 kilograms of vapor per kilogram of said aromatic compound fed to said oxidizer, wherein said oxidizer off-gas comprises at least about 50 weight percent of vapor compounds including vaporized water and vaporized hydrocarbyl compounds, wherein said oxidizing is performed at a temperature of from 140 to 170° C. at a pressure of less than 8 bara;
(b) recovering hydrocarbyl compounds from said oxidizer off-gas in a solvent recovery system to thereby produce a hydrocarbyl-depleted off-gas comprising at least 3.3 kilograms of water vapor per kilogram of said aromatic compound fed to said oxidizer; and
(c) passing at least a portion of said hydrocarbyl-depleted off-gas through at least one turboexpander to thereby generate work, wherein said hydrocarbyl-depleted off-gas fed to said turboexpander comprises at least 3.3 kilograms of water vapor per kilogram of said aromatic compound fed to said oxidizer, wherein the mass of water vapor passed through said turboexpander is at least 50 percent of the amount of the mass of water exiting said solvent recovery system in said hydrocarbyl-depleted off-gas stream.

21. The process according to claim 20 wherein said hydrocarbyl-depleted off-gas is not subjected to thermal oxidative destruction (TOD) prior to entering said turboexpander.

22. The process according to claim 20 further comprising returning at least a portion of the recovered hydrocarbyl compounds to said oxidizer as recovered solvent.

23. The process according to claim 22 wherein at least 40 weight percent of said recovered solvent is supplied to said oxidizer at a temperature within 80° C. of the temperature of said oxidizer off-gas.

24. The process according to claim 20 further comprising subjecting a slurry comprising solid particles of said aromatic dicarboxylic acid and liquid solvent to solid-liquid separation and/or washing, further comprising recovering a filtrate solvent from said solid-liquid separation and/or washing step and returning at least a portion of said filtrate solvent to said oxidizer.

25. The process according to claim 24 wherein at least 40 weight percent of said filtrate solvent supplied to said oxidizer enters said oxidizer at a temperature of at least about 60° C.

26. The process according to claim 20 further comprising compressing air in an air compressor and feeding the resulting compressed air to said oxidizer.

27. The process according to claim 26 wherein said air compressor is at least partly powered by said turboexpander.

28. The process according to claim 27 wherein a turboexpander off-gas is discharged from said turboexpander, wherein the discharge pressure of said turboexpander off-gas is at least 0.05 barg and less than about 0.9 barg.

* * * * *